(12) United States Patent
Choi et al.

(10) Patent No.: US 10,004,468 B2
(45) Date of Patent: Jun. 26, 2018

(54) X-RAY IMAGING DEVICE AND X-RAY IMAGING METHOD

(71) Applicants: Vatech Co., Ltd., Gyeonggi-do (KR); Vatech Ewoo Holdings Co., Ltd., Gyeonggi-do (KR)

(72) Inventors: Sung Il Choi, Gyeonggi-do (KR); Byung Jun Ahn, Gyeonggi-do (KR); Sang Baek Noh, Gyeonggi-do (KR); Chi Twak Oh, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 118 days.

(21) Appl. No.: 14/913,683

(22) PCT Filed: Aug. 20, 2014

(86) PCT No.: PCT/KR2014/007742
§ 371 (c)(1),
(2) Date: Feb. 22, 2016

(87) PCT Pub. No.: WO2015/026165
PCT Pub. Date: Feb. 26, 2015

(65) Prior Publication Data
US 2016/0199014 A1 Jul. 14, 2016

(30) Foreign Application Priority Data

Aug. 20, 2013 (KR) .......................... 10-2013-0098642

(51) Int. Cl.
*A61B 6/14* (2006.01)
*A61B 6/00* (2006.01)
(Continued)

(52) U.S. Cl.
CPC ............ *A61B 6/4452* (2013.01); *A61B 6/032* (2013.01); *A61B 6/14* (2013.01); *A61B 6/4441* (2013.01);
(Continued)

(58) Field of Classification Search
CPC ......... A61B 6/14; A61B 6/4452; A61B 6/466; A61B 6/5205; A61B 6/032; A61B 6/506;
(Continued)

(56) References Cited

U.S. PATENT DOCUMENTS 5,305,368 A    4/1994   Bisek et al.
5,355,398 A *  10/1994  Nakano .................. A61B 6/032
                                                  378/38

(Continued)

FOREIGN PATENT DOCUMENTS

CN      102711622 A    10/2012
EP        1491145 A1   12/2004
(Continued)

OTHER PUBLICATIONS

European Patent Office, Supplementary European Search Report of EP Patent Application No. 14837639.5, Mar. 24, 2017.
(Continued)

*Primary Examiner* — Irakli Kiknadze
(74) *Attorney, Agent, or Firm* — IP Legal Services, LLC

(57) ABSTRACT

An X-ray imaging device and an X-ray imaging method for obtaining 3D X-ray images of an entire field of view (FOV). The device includes an X-ray source for radiating X-rays to a part of an FOV and an X-ray sensor for detecting the X-rays, which have passed through the part of the FOV. The X-ray sensor has a width narrower than the radius of a smallest circle including a cross section perpendicular to the longitudinal direction of the FOV. A rotating arm supports the X-ray source and the X-ray sensor to face each other
(Continued)

with the FOV therebetween. The rotating arm rotates and moves about an axis of rotation between the X-ray source and the X-ray sensor so that the X-rays are radiated to the entire area of the FOV in various directions of the FOV.

18 Claims, 14 Drawing Sheets

(51) Int. Cl.
*G06T 7/00* (2017.01)
*G06T 15/00* (2011.01)
*G06T 15/08* (2011.01)
*A61B 6/03* (2006.01)

(52) U.S. Cl.
CPC ............ *A61B 6/466* (2013.01); *A61B 6/5205* (2013.01); *G06T 7/0012* (2013.01); *G06T 15/005* (2013.01); *G06T 15/08* (2013.01); *A61B 6/035* (2013.01); *A61B 6/463* (2013.01); *G06T 2200/04* (2013.01); *G06T 2207/10116* (2013.01); *G06T 2207/30036* (2013.01)

(58) Field of Classification Search
CPC ......... A61B 6/027; A61B 6/4085; A61B 1/24; A61B 5/1077; A61B 5/4547; A61B 5/7435; A61B 6/025; A61B 6/04; A61B 6/0421; A61B 6/4233; A61B 6/469; A61B 6/481; A61B 6/504; G06T 15/005; G06T 15/08; G06T 2200/04; G06T 2207/10116; G06T 2207/30036; G06T 7/0012; G01N 2223/419; G01N 23/046; H05G 1/44; H05G 1/64
USPC ...................................... 378/38, 39, 168, 191
See application file for complete search history.

(56) References Cited

U.S. PATENT DOCUMENTS

| | | | | |
|---|---|---|---|---|
| 6,018,563 | A * | 1/2000 | Arai | A61B 6/14 378/39 |
| 7,787,586 | B2 * | 8/2010 | Yoshimura | A61B 6/032 378/38 |
| 2001/0036246 | A1 * | 11/2001 | Graumann | A61B 6/0478 378/39 |
| 2003/0235265 | A1 | 12/2003 | Clinthorne et al. | |
| 2004/0066877 | A1 | 4/2004 | Arai et al. | |
| 2005/0117693 | A1 * | 6/2005 | Miyano | A61B 6/0478 378/4 |
| 2005/0117696 | A1 | 6/2005 | Suzuki et al. | |
| 2006/0067464 | A1 | 3/2006 | Clinthorne et al. | |
| 2006/0203959 | A1 * | 9/2006 | Spartiotis | A61B 6/14 378/38 |
| 2008/0118024 | A1 | 5/2008 | Cho et al. | |
| 2009/0310845 | A1 * | 12/2009 | Ogawa | A61B 6/14 382/132 |
| 2010/0054403 | A1 | 3/2010 | Ro et al. | |
| 2012/0020450 | A1 | 1/2012 | Jung et al. | |
| 2012/0025088 | A1 | 2/2012 | Nakayama | |
| 2012/0307960 | A1 | 12/2012 | Choi et al. | |
| 2012/0314835 | A1 | 12/2012 | Mueller | |
| 2013/0114799 | A1 | 5/2013 | Yamakawa et al. | |
| 2013/0177213 | A1 | 7/2013 | Lee et al. | |
| 2015/0305696 | A1 | 10/2015 | Yamakawa et al. | |

FOREIGN PATENT DOCUMENTS

| | | |
|---|---|---|
| JP | 10-052423 A | 2/1998 |
| JP | 2006-325978 A | 12/2006 |
| JP | 2012-024516 A | 2/2012 |
| JP | 2013-135765 A | 7/2013 |
| KR | 10-2006-0085310 A | 7/2006 |
| KR | 10-2008-0054702 A | 6/2008 |
| KR | 10-2010-0070160 A | 6/2010 |
| KR | 10-2010-0070817 A | 6/2010 |
| KR | 10-2010-0070822 A | 6/2010 |
| KR | 10-2011-0083153 A | 7/2011 |
| KR | 10-2012-0010639 A | 2/2012 |
| KR | 10-2013-0018896 A | 2/2013 |
| KR | 10-2013-0081798 A | 7/2013 |
| WO | 2012/008492 A1 | 1/2012 |

OTHER PUBLICATIONS

European Patent Office, European Search Opinion of EP Patent Application No. 14837639.5, Mar. 24, 2017.
European Patent Office, Supplementary European Search Report of EP Patent Application No. 14838466.2, dated Mar. 24, 2017.
European Patent Office, European Search Opinion of EP Patent Application No. 14838466.2, dated Mar. 24, 2017.

* cited by examiner (a)                    (b)

X-RAY IMAGING DEVICE AND X-RAY IMAGING METHOD

CROSS REFERENCE TO RELATED APPLICATIONS

This application is a National Stage Patent Application of PCT International Patent Application No. PCT/KR2014/007742 (filed on Aug. 20, 2014) under 35 U.S.C. § 371, which claims priority to Korean Patent Application No. 10-2013-0098642 (filed on Aug. 20, 2013), the teachings of which are incorporated herein in their entireties by reference.

TECHNICAL FIELD

The present invention generally relates to X-ray imaging. More particularly, the present invention relates to an X-ray imaging device and an X-ray imaging method, in which a three-dimensional image of an entire field of view (FOV) is rendered using an X-ray sensor having a small width, the width being less than the radius of a smallest circle including a cross-section perpendicular to the longitudinal direction of the FOV.

BACKGROUND ART

X-rays attenuate while passing through an object, depending on the X-ray attenuation coefficient unique to the object, such as Compton scattering or photoelectric effect.

X-ray imaging is radiography using the transmission characteristics of X-rays, and renders an X-ray image of the internal structure of a field of view (FOV) of a subject, based on the amount of X-rays attenuated during transmission of the FOV. In this regard, an X-ray imaging device includes an X-ray source emitting X-rays to the FOV, an X-ray sensor detecting X-rays that have passed through the FOV, and an image processor rendering an X-ray image of the FOV based on the X-ray detection result of the X-ray sensor.

Recently, while X-ray imaging is being rapidly substituted by digital radiography (DR) using a digital sensor, owing to the development of semiconductors and information processing technologies, a variety of improvements has been undertaken for X-ray imaging technology.

For example, FIG. 1 is a typical X-ray panoramic image of teeth and body portions surrounding the teeth, used in the dental field, and FIG. 2 is a conceptual view schematically illustrating a typical method of obtaining an X-ray panoramic image.

An X-ray panoramic image is obtained by obtaining X-ray images of the track of the dental arch of a subject while moving the X-ray source 4 and the X-ray sensor 5 on both sides of an FOV 2, i.e. the dental arch portion of a subject, to face each other, combining the obtained X-ray images, and deploying and displaying the relationship of the arrangement of teeth and body portions surrounding the teeth in a single transmission image. Thus, the X-ray panoramic image is used as a standard image most familiar to dentists, since the relationship of the overall arrangement of teeth and body portions surrounding the teeth can be easily viewed.

In order to obtain the panoramic image, a rotary shaft 3 between the X-ray source 4 and the X-ray sensor 5 has a two-axis drive system, i.e. the rotary shaft 3 linearly moves to a predetermined range of length while rotating to a predetermined range of angle. With this configuration, a focal range defined at a point between the rotary shaft 3 and the X-ray sensor 5 is moved on the track of the dental arch for scanning, such that the detection result of X-rays of teeth and body portions surrounding the teeth according to the sections of the track of the dental arch are obtained.

However, the X-ray panoramic image has problems of the transmission image, such as low accuracy of information regarding lengths, teeth overlapping, or blurring caused by the cervical vertebrae.

In another example, FIG. 3 is an X-ray CT image of a typical head, X-ray CT being used in the dental and related surgical fields, and FIG. 4 is a conceptual view schematically illustrating a typical method of obtaining an X-ray CT image.

An X-ray CT image is obtained by obtaining X-ray images by rotating the X-ray source 4 and the X-ray sensor 5 disposed on both sides of the FOV 2, i.e. the head of a subject, to face each other, and reconstructing the result of X-ray image obtaining using a reconstruction algorithm. Thus, a 3D image of the FOV is displayed. It is therefore possible to accurately display not only a 3D image (corresponding to the right bottom part of FIG. 3) of the entire FOV but also topographic images (corresponding to the left top and bottom parts and the right top part of FIG. 3) according to positions and directions desired by a user. Accordingly, X-ray CT images are used by dentists in areas such as implant surgeries, where a high degree of precision is required.

In addition, in order to obtain X-ray CT image as described above, the rotary shaft 3 between the X-ray source 4 and the X-ray sensor 5 rotates in a range of angles, fixed to the rotary axis extending in the longitudinal direction of the FOV 2, which is referred to as single-axis drive. Consequently, detection results of X-rays are obtained in several directions of the entire FOV 2 having the shape of a cylinder, defined by the rotation of the tangent between the X-ray source 4 and the X-ray sensor 5 on both sides of the rotary shaft 3.

However, a typical X-ray CT image emits a relatively large amount of radiation to the FOV compared to an X-ray panoramic image, and requires an X-ray sensor having a larger area, in particular, a larger width, which is problematic.

More specifically, the X-ray sensor must detect X-rays that have passed through the entire area of the FOV in several directions of the FOV in order to obtain a typical X-ray CT image.

A case of obtaining an X-ray CT image in an FOV having a first width w1 (the maximum width of the FOV) and a first height t1 (the maximum height of the FOV) using X-rays in the form of a cone beam, which is typically used in the dental field, will be described by way of example. FIG. 5 illustrates the corresponding case.

As illustrated in the drawing, in the case of typical X-ray CT image obtaining, the rotary shaft 3 between the X-ray source 4 and the X-ray sensor 5 rotates on a single axis in a range of angles, fixed to the center axis extending in the longitudinal direction of the FOV 2. Here, the second width w2 of the X-ray sensor 5 must be equal to or greater than the first width w1, i.e. w2≥(d2/d1)×w1, in which the magnification ratio d2/d1 of the X-ray imaging device, defined as the ratio of the distance d1 between the X-ray source 4 and the center axis of the FOV 2 with respect to the distance d2 between the X-ray source 4 and the X-ray sensor 5, is reflected, and the second height t2 of the X-ray sensor 5 must be equal to or greater than the first height t1, i.e. t2≥(d2/d1)×t1, in which the magnification ratio d2/d1 of the X-ray imaging device is reflected. Under these conditions, X-rays that have passed through the entire area of the FOV 2 in several direction of the FOV 2 can be detected. Thus, the FOV 2 has the shape of a cylinder having the first height, in which the diameter of the cross-section perpendicular to the longitudinal direction is the first width.

For reference, depending on the purpose, a half beam or half scan method may be used, on the assumption that the rotary shaft between the X-ray source and the X-ray sensor in X-ray CT image obtaining is identical to the center axis extending in the longitudinal direction of the FOV. In the half beam or half scan method, the second width w2 of the X-ray sensor is reduced to w$2 \geq (d2/d1) \times$w/2 using full width half maximum (FWHM) asymmetric X-rays that transmit one of the left FOV and the right FOV of the rotary shaft.

However, regardless of which method is used, the width of the CT image-obtaining X-ray sensor must be equal to or greater than the radius of a circle, the cross-section of which is perpendicular to the longitudinal direction of the FOV, in order to render a 3D image of the entire FOV. Thus, the width of the CT image-obtaining X-ray sensor is significantly larger than the width of the panoramic image-obtaining X-ray sensor.

In fact, when attempting to obtain an X-ray panoramic image and an X-ray CT image in the same FOV, the panoramic image-obtaining X-ray sensor has the shape of a slit, the width thereof ranging from 5 mm to 20 mm, whereas the CT image-obtaining X-ray sensor has the shape of a square or a similar shape, the width thereof being similar to the height thereof.

In addition, the price of a typical X-ray sensor significantly increases with the size. The high price of the X-ray CT device is unavoidable due to the X-ray sensor having a large width. In addition, as the area of the X-ray sensor increases, the amount of radiation emitted to a subject also increases, which is problematic.

DISCLOSURE

Technical Problem

Accordingly, the present invention is intended to propose an X-ray imaging device and an X-ray imaging method, in which a three-dimensional image of an entire field of view (FOV) is rendered using an X-ray sensor having a small width, the width being less than the radius of a smallest circle having a cross-section perpendicular to the longitudinal direction of the FOV.

Technical Solution

In order to achieve the above object, according to one aspect of the present invention, there is provided an X-ray imaging device including: an X-ray source configured to emit X-rays to a portion of a field of view; an X-ray sensor configured to detect the X-rays that have passed through the portion of the field of view; a moving unit configured to move at least one of the X-ray source and the X-ray sensor such that the X-ray source emits the X-rays in several directions of the field of view to pass through substantially the entire portions of the field of view and the X-ray sensor receives the X-rays that have passed through substantially the entire portions of the field of view; and an imaging processor configured to render a three-dimensional image of the entire field of view based on X-rays that have passed through substantially the entire portions of the field of view and have been detected by the X-ray sensor.

Here, the portion of the FOV may be less than a half of the FOV. In addition, the X-ray sensor may have a width less than a radius of a smallest circle including a cross-section perpendicular to a longitudinal direction of the FOV multiplied by a magnification ratio.

Furthermore, the moving unit may include a rotary arm supporting the X-ray source and the X-ray sensor such that the X-ray source and the X-ray sensor are disposed on both sides of the FOV to face each other, wherein the rotary arm rotates around a rotary shaft between the X-ray source and the X-ray sensor. The moving unit may include a rotary arm-moving unit moving the rotary shaft on a plane perpendicular to the rotary shaft in at least a section of X-ray image obtaining. The rotary arm-moving unit may move the rotary shaft on a curved track on the plane.

According to another aspect of the present invention, there is provided an X-ray imaging device including: an X-ray source emitting X-rays to a portion of a FOV; an X-ray sensor detecting X-rays that have passed through the portion of the FOV; a rotary arm supporting the X-ray source and the X-ray sensor such that the X-ray source and the X-ray sensor are disposed on both sides of the FOV to face each other, the rotary arm being rotatable around a rotary shaft between the X-ray source and the X-ray sensor; and a rotary arm-moving unit moving the rotary shaft on a plane perpendicular to the rotary shaft in at least a section of X-ray image obtaining.

Here, the rotary arm-moving unit may move the rotary shaft such that the X-ray source emits X-rays in several directions of the FOV to pass through substantially entire portions of the FOV and the X-ray sensor receives X-rays that have passed through substantially the entire portions of the FOV. Alternatively, the X-ray imaging device may further include a rotary arm support supporting the rotary arm by means of the rotary arm-moving part. The rotary arm-moving unit may include: a movable base connected to the rotary arm and rotatably disposed on the rotary arm support; a first driving unit moving the movable base with respect to the rotary arm support such that the rotary shaft moves on a curved track; and a second driving unit rotating the rotary shaft with respect to the movable base. Here, the rotary arm-moving unit may further include a curved rail disposed on the rotary arm support, the movable base being movable on the curved rail.

In addition, the rotary arm-moving unit may include: a connecting arm connected to the rotary arm and connected to the rotary arm shaft by means of a connecting shaft; a first driving unit rotating the connecting shaft with respect to the rotary arm support such that the rotary shaft moves on a curved track; and a second driving unit rotating the rotary shaft with respect to the connecting arm. Here, the X-ray imaging device may further include a shaft-adjusting portion moving at least one of the connecting shaft and the rotary shaft with respect to the connecting arm. The shaft-adjusting portion may adjust a distance between the connecting shaft and the rotary shaft.

Furthermore, the X-ray sensor may have a width less than a radius of a smallest circle, including a cross-section perpendicular to a longitudinal direction of the FOV, multiplied by a magnification ratio. The portion of the FOV may be less than a half of the FOV.

According to further another aspect of the present invention, there is provided an X-ray imaging method including: a) step of obtaining a detection result of X-rays that have passed through substantially entire portions of a FOV by emitting X-rays in several directions of the FOV to pass through substantially the entire portions of the FOV and detecting X-rays that have passed through substantially the entire portions of the FOV, each of the entire portions of the FOV being smaller than a half of the FOV; and b) step of rendering a three-dimensional image of the entire FOV based on the detection result of X-rays.

Here, b) step may include rendering the three-dimensional image by reconstructing the detection result of X-rays using a reconstruction algorithm. The reconstruction algorithm may include an iterative reconstruction algorithm based on compressed sensing or a filter back projection algorithm including back projection. The X-ray imaging method may further include a step of compensating for the detection result of X-rays such that position-specific reconstruction conditions of the FOV are uniform. The detection result of X-rays may be compensated for according to directions in which X-rays pass through the FOV.

The reconstruction conditions may include at least one of a magnification ratio of the detection result of X-rays and a number of overlapping of X-rays in the FOV.

According to yet another aspect of the present invention, there is provided X-ray imaging method including: a step of determining directions of X-ray emissions in which X-rays are emitted to pass through portions of a FOV in several directions of the FOV, each of the portions of the FOV being smaller than a half of the FOV; emitting X-rays in the directions of X-ray emissions and obtaining a detection result of X-rays that have passed through the FOV; and rendering a three-dimensional area of the entire FOV based on the detection result of X-rays.

Here, the step of determining the directions of X-ray emissions may include determining the directions of X-ray emissions such that X-rays pass through substantially entire portions of the FOV. The step of determining the directions of X-ray emissions may include determining the directions of X-ray emissions such that a range of position-specific angles of X-ray emissions of the FOV is equal to or greater than a reference value. The reference value may be equal to or greater than 90° or 180° and may be smaller than 360°.

Advantageous Effects

According to the present invention having the above-described characteristics, the X-ray imaging device and the X-ray imaging method render a 3D image of the entire FOV by emitting X-rays in several directions such that X-rays pass portions of the FOV. It is thereby possible to render a precise 3D image of the entire FOV using an X-ray sensor having a smaller width than those of existing X-ray CT image-obtaining sensors. In particular, the width of the X-ray sensor used herein is less than the radius of a smallest circle including a cross-section perpendicular to the longitudinal direction of the FOV.

In addition, in the X-ray imaging method and the X-ray imaging device according to the present invention, the possibility of a physical interference, such as a collision, between the X-ray source or the X-ray sensor and the subject during X-ray image obtaining is removed, the ease of control in response to mechanical movement of the X-ray source and the X-ray sensor is maximized, and any factors, such as vibration, that may lower the reliability of X-ray images are minimized. Accordingly, it is possible to advantageously obtain X-ray images in a more safe and reliable manner.

MODE FOR INVENTION

Reference will now be made in greater detail to exemplary embodiments of the present invention. For reference, dental X-ray imaging will be described by way of example, and the concept of the present invention is not limited thereto. It will be apparent to a person skilled in the art from the following description that the concept of the present invention is applicable to all types of X-ray imaging.

Prior to full description, the major characteristics of an X-ray imaging method according to the present invention will be discussed first with reference to the relevant drawings for better understanding.

Figure 1:
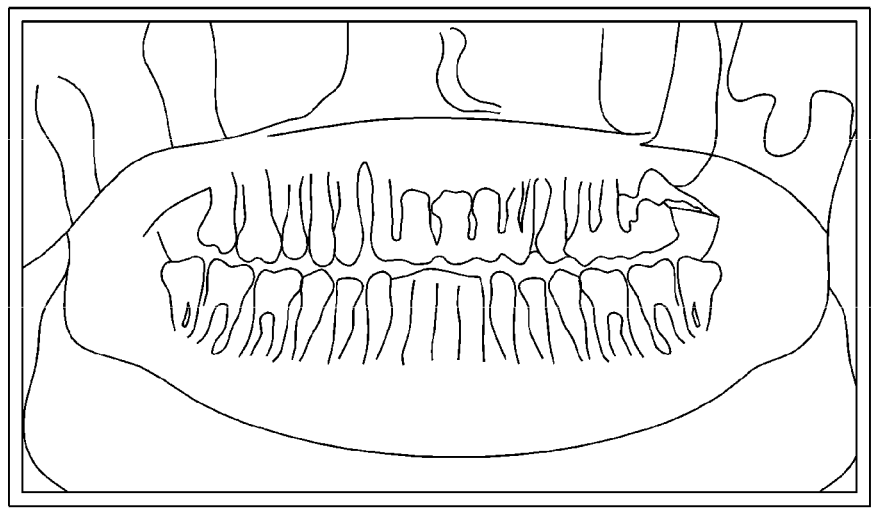
FIG. 1 is a typical X-ray panoramic image.
Figure 2:
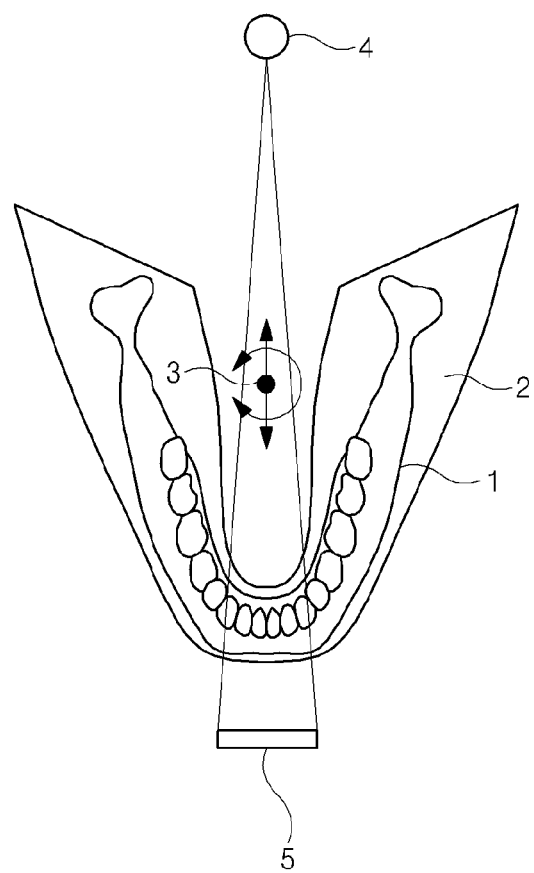
FIG. 2 is a conceptual view schematically illustrating a typical method of obtaining an X-ray panoramic image.
Figure 3:
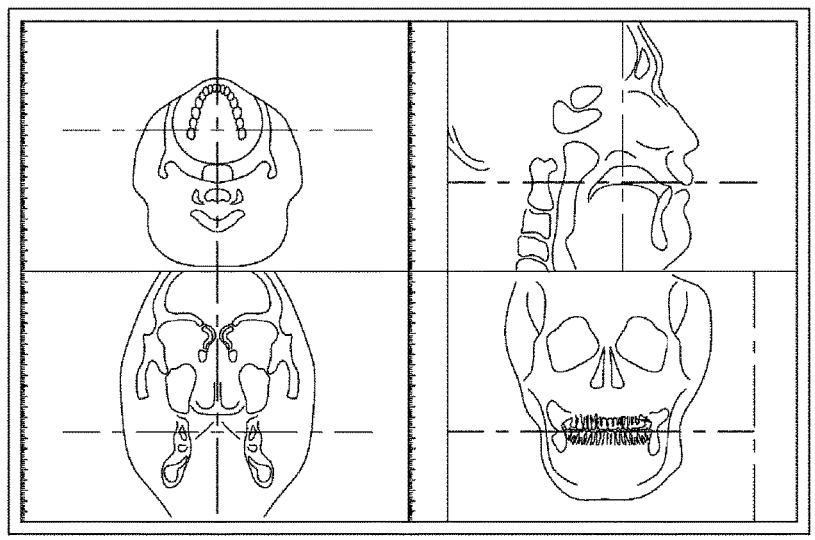
FIG. 3 is a typical X-ray CT image.
Figure 4:
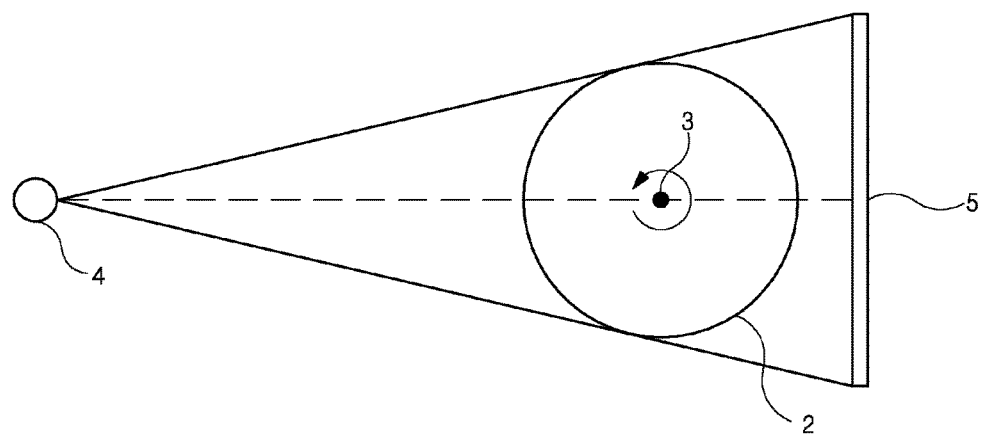
FIG. 4 is a conceptual view illustrating a typical method of obtaining an X-ray CT image.
Figure 5:
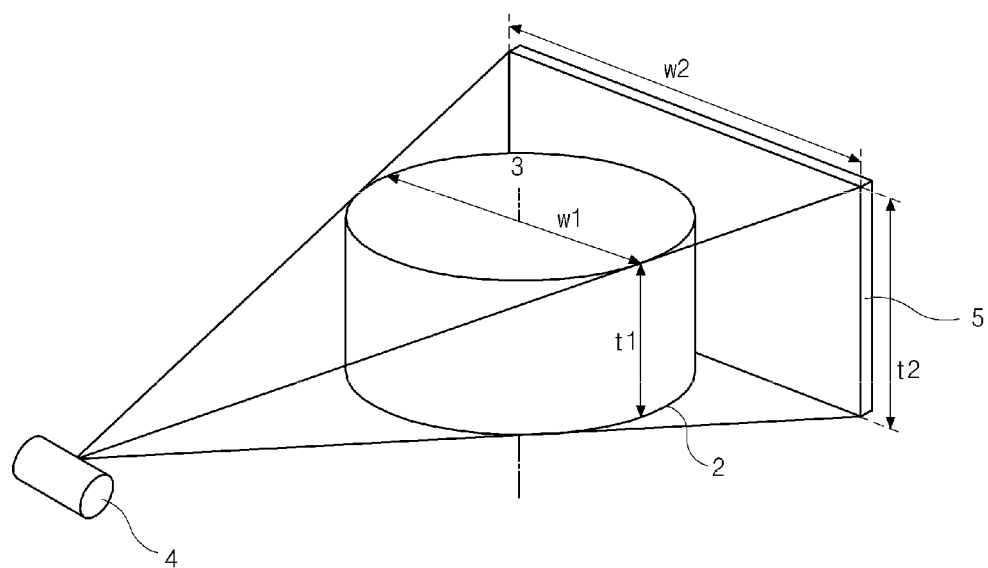
FIG. 5 is a conceptual view illustrating a field of view (FOV) area in a typical method of obtaining an X-ray CT image and the relationship between an X-ray source and an X-ray sensor.
Figure 6:
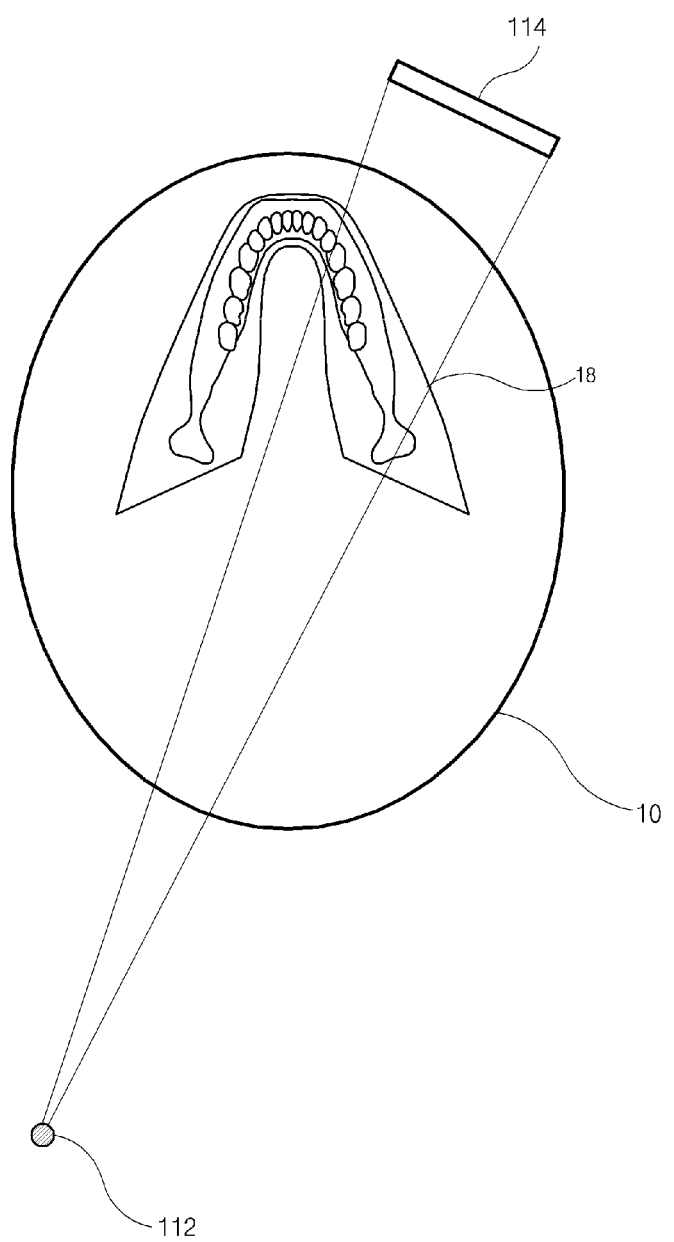
FIG. 6 is a conceptual view illustrating an X-ray imaging method according to the present invention.
Figure 7:
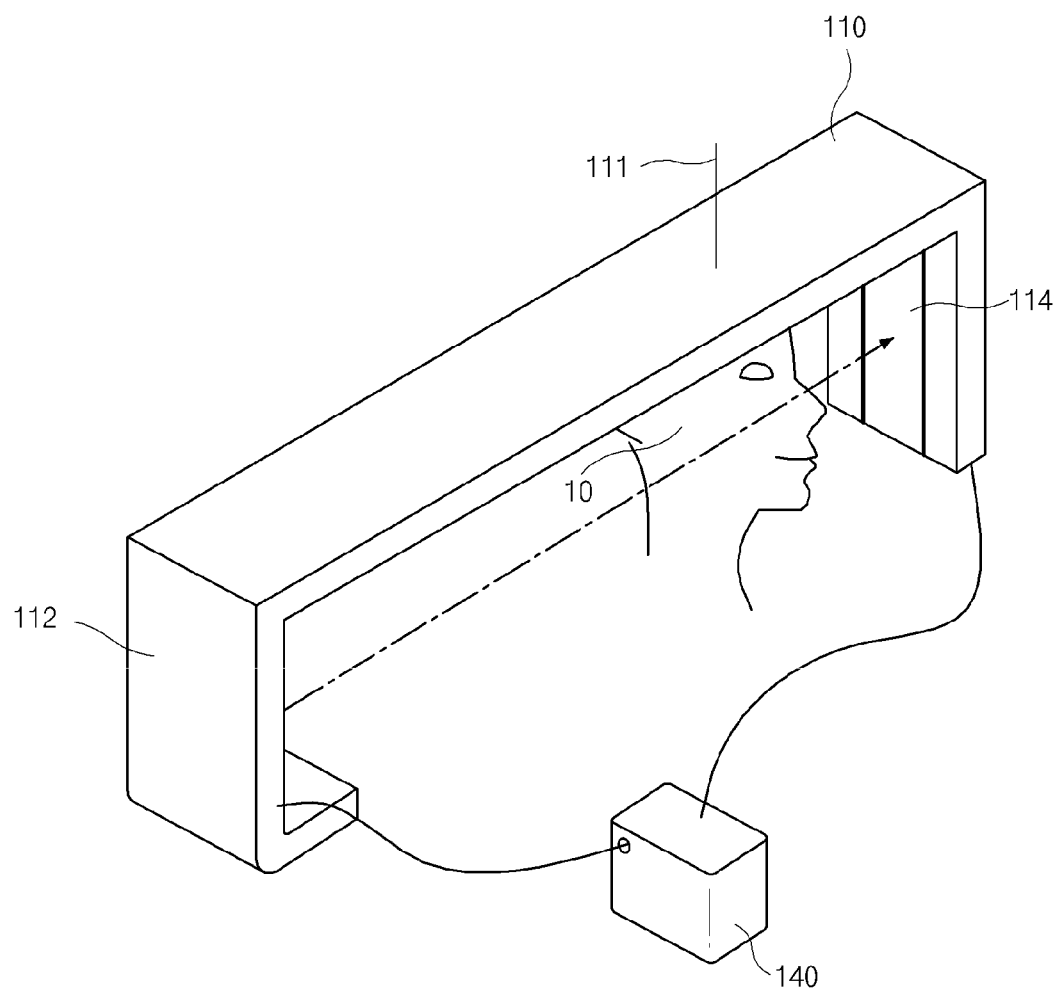
FIG. 7 is a conceptual view illustrating an X-ray imaging device according to the present invention.

FIG. 6 is a conceptual view schematically illustrating the relationship among an FOV 18, an X-ray source 112, and an X-ray sensor 114 in an X-ray imaging method according to the invention, and FIG. 7 is a conceptual view illustrating a schematic configuration for performing the X-ray imaging method according to the present invention.

As illustrated in the drawings, the X-ray imaging method according to the present invention uses the X-ray source 112 emitting X-rays to portions of the FOV 18 in several directions of the FOV 18, an X-ray sensor 114 detecting X-rays that have passed through a portion of the FOV 18 in several directions of the FOV 18, and an image processor 140 rendering a three-dimensional (3D) image of the entire FOV 18 based on the result of detection by the X-ray sensor 114. For reference, herein, the FOV 18 consistently means a field of view (FOV), i.e. a 3D FOV.

The X-ray source 112 includes an adjusting means, such as a collimator, that controls the angle of emission and the area of emission of X-rays. The X-ray source 112 emits X-rays corresponding to the X-ray sensor 114, which will be described later, to a portion of the FOV 18, more particularly, a portion of the FOV 18 less than the half of the entire area of the FOV 18, in several directions of the FOV 18, using the adjusting means. In addition, the X-ray sensor 114 has a predetermined width, more particularly, a width less than the radius of a smallest circle, including a cross-section perpendicular to the longitudinal direction of the FOV 18, multiplied by a magnification ratio (radius×magnification ratio). The X-ray sensor 114 is disposed facing the X-ray source 112 to detect X-rays that have passed through the portion of the FOV 18 less than the half of the entire area of the FOV 18, in several directions of the FOV 18.

In this regard, at least one of the X-ray source 112 and the X-ray sensor 114 can be moved using a moving part. It is preferable that the X-ray source 112 and the X-ray sensor 114 are mount both ends of a rotary arm 110 such that the X-ray source 112 and the X-ray sensor 114 move while facing each other. The rotary arm 110 is a structural shape of an arm or a gantry. In this regard, the rotary arm 110 includes a rotary shaft 111 between the X-ray source 112 and the X-ray sensor 114. The rotary shaft 111 moves along a plane crossing the rotary shaft 111 while rotating within a predetermined range of angle in at least a partial section of X-ray imaging. The rotation and movement of the rotary shaft 111 will be discussed in detail in the corresponding unit of the description.

When the X-ray imaging method according to the present invention is used for dentistry, the FOV 18 may be, for example, a partial area of a head 10 including a dental arch of a subject. That is, as illustrated in the drawings, the cross-section of the FOV 18 perpendicular to the longitudinal direction thereof may have the shape of an arch or a horse's hoof including the dental arch. However, this is not intended to be limiting. In the X-ray imaging method according to the present invention, the cross-section of the FOV 18 perpendicular to the longitudinal direction thereof may be modified into a variety of diagrams, such as a circle, an ellipse, and an arc, depending on the purpose. Regardless of the shape of the FOV 18, the width of the X-ray sensor 114 is less than the radius of a smallest circle, including a cross-section perpendicular to the longitudinal direction of the FOV 18, multiplied by a magnification ratio.

Consequently, the X-ray imaging method according to the present invention renders a 3D image of the entire FOV 18 by emitting and detecting X-rays, which is passing through portions of the FOV 18, to the entire area of the FOV 18 in several directions of the FOV 18. In this regard, the X-ray imaging method according to the present invention is characterized by defining the position-specific directions of emission of X-rays required for rendering the 3D image of the FOV 18.

More specifically, since the X-ray imaging method according to the present invention uses X-rays in several directions, the X-rays passing through the portions of the FOV 18, the X-rays may be emitted in different position-specific directions of the FOV 18. In addition, X-rays must be emitted in a predetermined range of angles over substantially the entire area of the FOV 18 in order to realize a 3D image by reconstructing the detection result of X-rays. Although the range of angles of X-ray emissions varies depending on the reconstruction algorithm, it is reported that the range of angles of X-ray emissions is equal to or greater than 90° when an iterative reconstruction algorithm based on compressed sensing (CS) is used and to be equal to or greater than 180° when a filter back projection (FBP) algorithm including back projection (BP), a typical example of an analytic method, is used.

However, since the X-ray imaging method according to the present invention causes X-rays to pass through the portions of the FOV 18 in several directions of the FOV 18, the position-specific angles of X-ray emissions may differ, thereby causing the range of angles of X-ray emissions required for 3D imaging to be significantly different or insufficient.

Thus, the X-ray imaging method according to the present invention is characterized by determining position-specific directions of X-ray emissions for the 3D imaging of the FOV 18, by considering all directions of X-rays passing through the portions of the FOV 18, thereby obtaining the range of angles of X-ray emissions required for 3D imaging, over substantially the entire area of the FOV 18.

Figure 8:
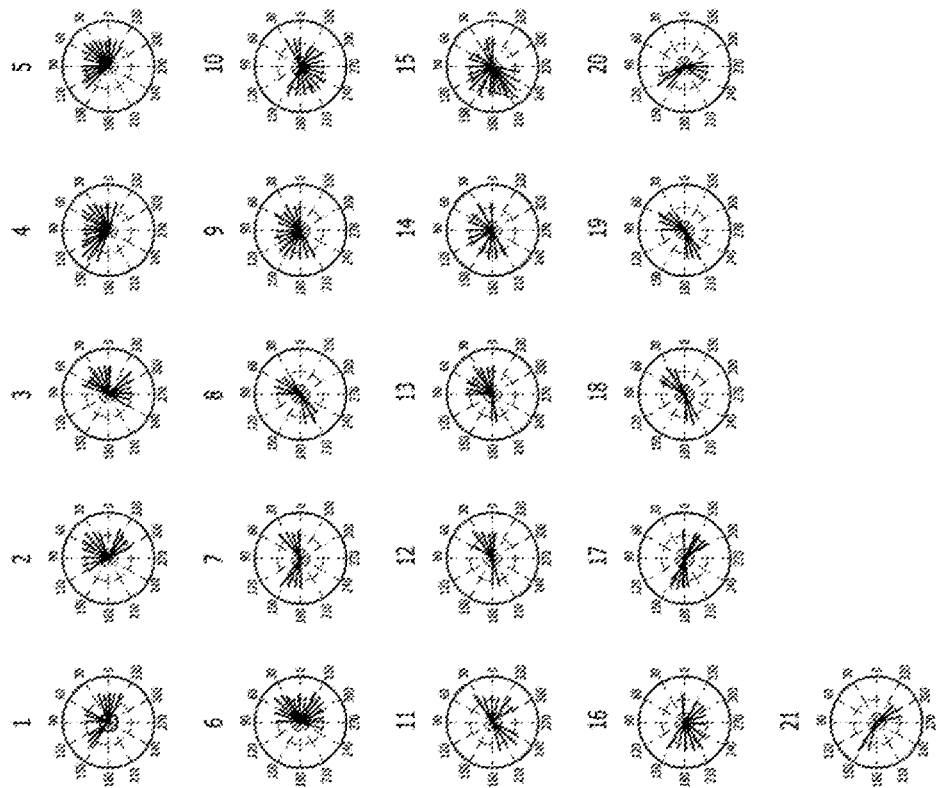
FIG. 8 is a conceptual view illustrating the range of position-specific angles of X-ray emissions required for 3D imaging of an FOV.
Figure 8:
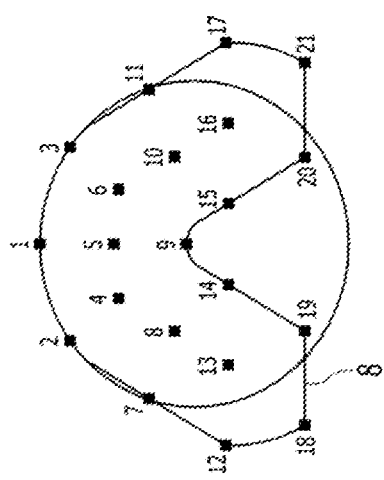

FIG. 8 illustrates the range of position-specific angles of X-ray emissions required for 3D imaging in the X-ray imaging method according to the present invention.

Here, the range of angles of X-ray emissions is determined considering all directions of X-rays passing through the portions of the FOV 18. The position-specific directions of X-ray emissions of the FOV 18 are determined such that the range of angles of X-ray emissions over substantially the entire area of the FOV 18 is equal to or greater than a reference value. For reference, the reference value of the range of angles of X-ray emissions may be equal to or greater than 90° or 180° and may be equal to or smaller than 360°.

Figure 9:
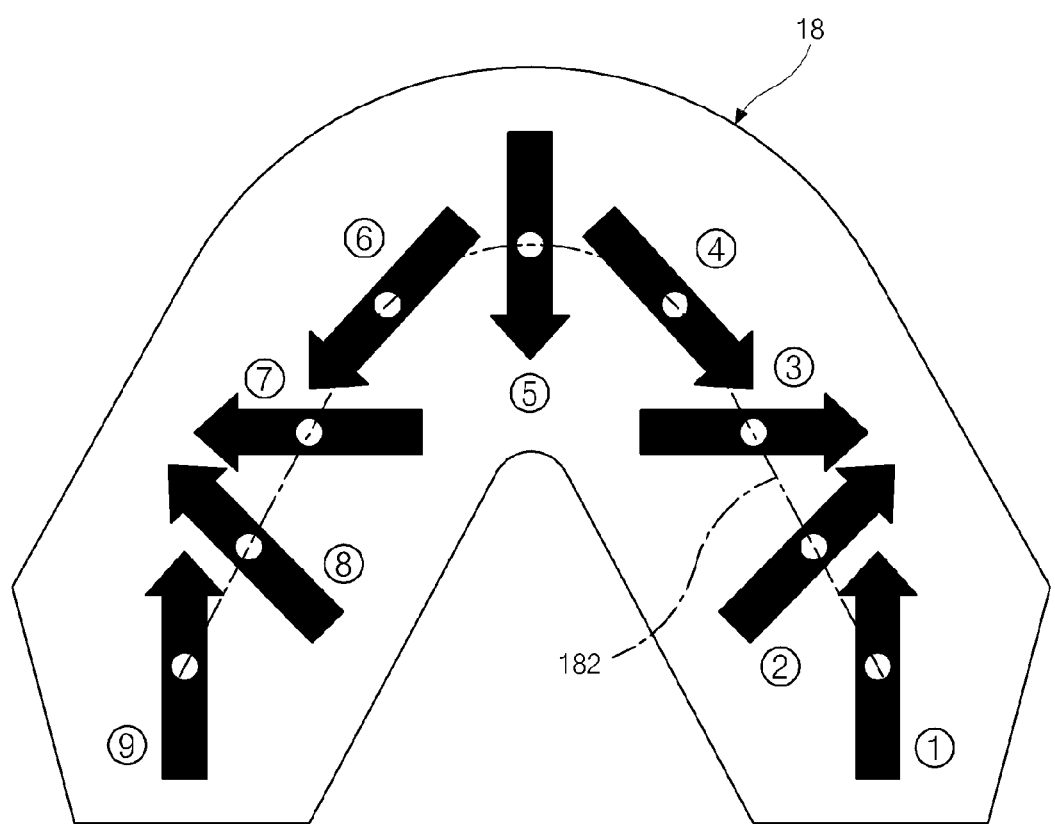
FIG. 9 is a conceptual view illustrating position-specific directions of X-ray emissions for 3D imaging of an FOV.

FIG. 9 is a conceptual view illustrating the position-specific directions of X-ray emissions for 3D imaging of the FOV 18 in the X-ray imaging method according to the present invention. For reference, in FIG. 9, arrows indicating the position-specific directions of X-ray emissions are marked on a track 182 of the dental arch on the assumption that the FOV 18 has the shape of an arch or a horse's hoof including the dental arch of a subject, and are designated with ① to ⑨ for the sake of brevity. The directions indicated by the arrows correspond to the directions of X-ray emissions.

Referring to the point ② at random, portions of X-rays passing through different points of the FOV 18, i.e. at least the points ①, ③, ④, and ⑦ in FIG. 9, pass through the point ②, although the passage of X-rays may differ more or less depending on the area on which X-rays are emitted. In other words, it will be apparent that a portion of the range of X-ray emission required for 3D imaging at the point ② is satisfied by X-rays passing through the other points. Thus, the arrows in FIG. 9 can be understood as briefly marking the position-specific directions of X-ray emissions of the FOV 18 for 3D imaging on the track 182 of the dental arch, considering X-rays passing through portions of the FOV 18 in all directions and the range of angles of X-ray emissions required for 3D imaging.

When the position-specific directions of X-ray emissions for 3D imaging of the FOV 18 are defined as described above, the rotary shaft between the X-ray source and the X-ray sensor is properly moved and rotated such that the arrows are aligned with the directions of X-ray emissions at points ① to ⑨. In this case, the range of the position-specific angles of X-ray emissions required for 3D imaging can be satisfied.

However, this is obtained by considering only the directions of X-ray emissions. In actual image obtaining, the subject may physically interfere with the X-ray source and/or the X-ray sensor and the X-ray source and the X-ray sensor may unnecessarily rotate and move, thereby lowering the efficiency of image obtaining.

Thus, the X-ray imaging method according to the present invention is further characterized by defining the position-specific directions of X-ray emissions required for 3D imaging of the FOV 18 and then determining a track on which the rotary shaft moves between the X-ray source and the X-ray sensor by projecting the position-specific directions of X-ray emissions to at least one curved track 160c.

Figure 10:
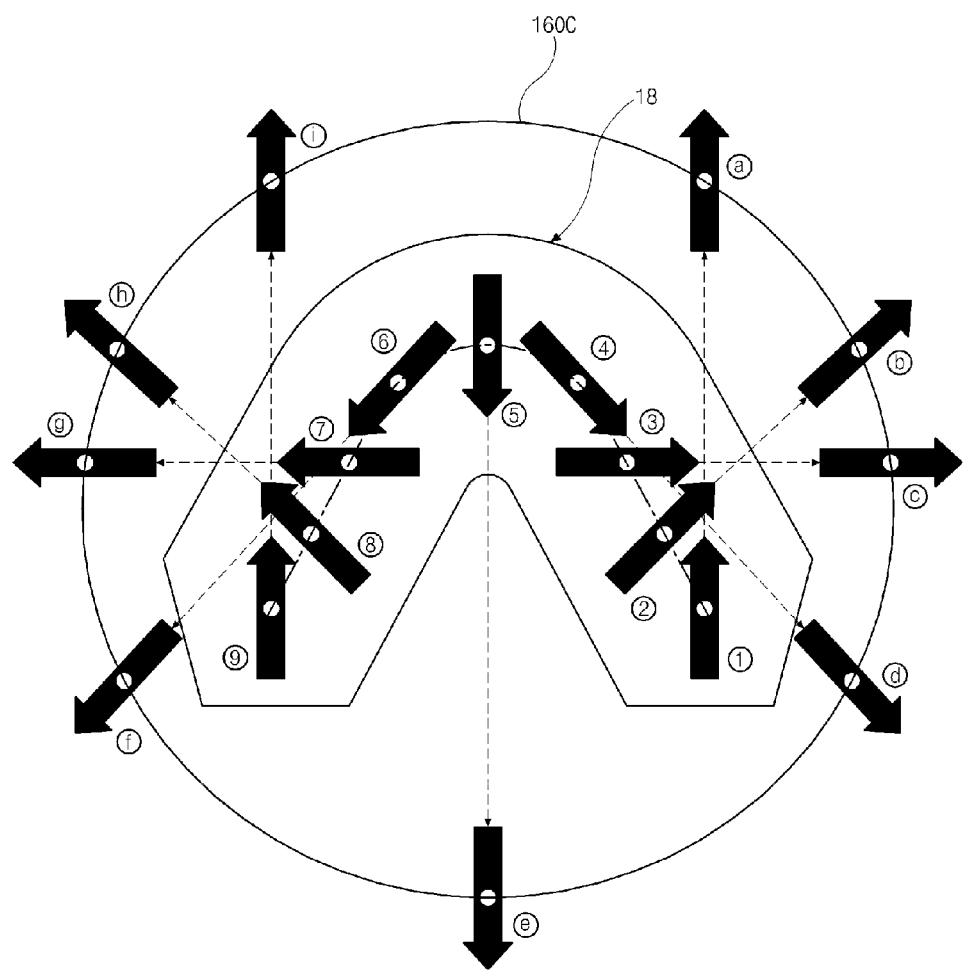
FIG. 10 is a conceptual view illustrating a process of projecting position-specific directions of X-ray emissions, required for 3D imaging of an FOV, to a curved track.
Figure 11:
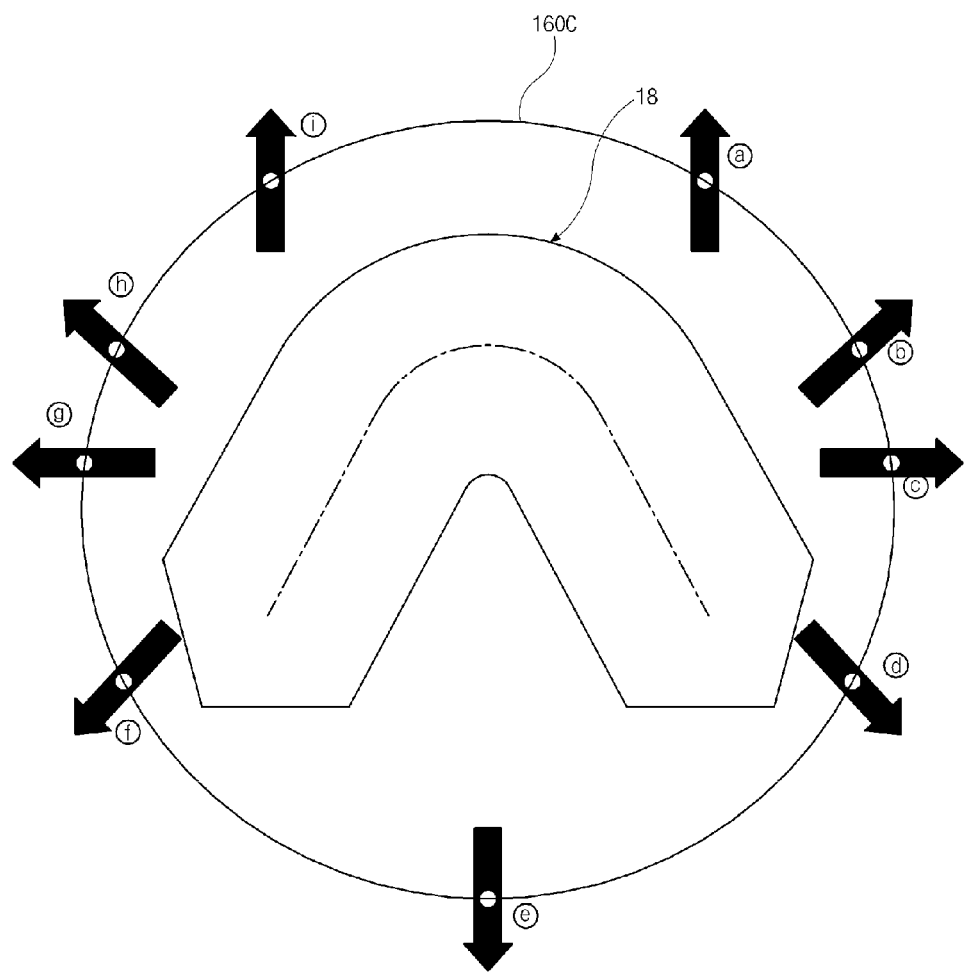
FIG. 11 is a conceptual view illustrating a result of projecting the position-specific directions of X-ray emissions, required for 3D imaging of the FOV, to the curved track.

FIG. 10 and FIG. 11 are conceptual views schematically illustrating a process of projecting the position-specific directions of X-ray emissions, required for 3D imaging of the FOV 18, to the at least one curved track 160c in the X-ray imaging method according to the present invention, and a result of the process.

As illustrated in FIG. 10, the X-ray imaging method according to the present invention projects X-rays by extending the predefined position-specific directions of X-ray emissions of the FOV 18 in the corresponding directions such that the position-specific directions of X-ray emissions cross the at least one curved track 160c. Referring to the drawings, it can be appreciated that the directions of X-ray emissions at the points ① to ⑨ are projected to points ⓐ to ⓘ on the at least one curved track 160c, in a one-to-one relationship.

Although it is illustrated in FIG. 10 that the position-specific directions of X-ray emissions of the FOV 18 are projected to cross the single curved track 160c, this is not intended to be limiting. Specifically, the curved track 160c may have the shape of a closed curve, such as a circle or an ellipse, in which the starting point meets the endpoint, or an open curve, in which the starting point is separated from the endpoint, or may be one or more tracks having different sizes and shapes, which are positioned within or outside of the FOV 18 or cross the FOV 18. For example, the number and size of the curved track 160c may be adjusted properly on the assumption that substantially all of the predefined position-specific directions of X-ray emissions of the FOV 18 are projected across the curved track 160c.

In an X-ray imaging device according to the present invention, which will be described later, the curved track 160c forms a track on which the rotary shaft actually moves between the X-ray source and the X-ray sensor. Thus, the curved track 160c needs to be designed to remove the possibility of physical interference, such as collision, with a subject, maximize the ease of control in response to mechanical movement of the X-ray source and the X-ray sensor, and minimize any factors, such as vibration, that may lower the reliability of X-ray images.

In this regard, the curved track 160c represents concentric circles, including two or less circular tracks having different sizes, or similar shapes. The movement and rotation of the rotary shaft on the circular tracks are defined in a single direction without conversion to the opposite direction.

Thus, as illustrated in FIG. 11, substantially the entire position-specific directions of X-ray emissions required for 3D imaging of the FOV 18 may be projected across the curved track 160c. In addition, at least one curved track 160c forms a track on which the rotary shaft moves between the X-ray source and the X-ray sensor in the X-ray imaging device according to the present invention, which will be described later.

When the at least one curved track 160c is determined as described above, X-ray images are obtained in the directions of X-ray emissions projected to the curved track 160c by properly rotating the X-ray source and the X-ray sensor while moving the rotary shaft on the curved track 160c. X-rays that have passed through portions of the FOV 18 in corresponding positions are detected.

The detection result of X-rays obtained as described above is the result of obtaining X-rays that have transmitted the entire area of the FOV 18 according to portions of the FOV 18 in several directions of the FOV 18, accurately, portions of the FOV 18 respectively being less than the half of the FOV 18. The result satisfies the range of angles of X-ray emission required for 3D imaging over substantially the entire area of the FOV 18.

Thus, the detection result of X-rays can be rendered as a 3D image of the entire area of the FOV 18 through a reconstruction process performed by the image processor (see 140 in FIG. 7; the same applies hereinafter) of the X-ray imaging method according to the present invention. For this, the image processor 140 includes a reconstruction algorithm.

Since the X-ray imaging method according to the present invention uses X-rays, which have passed through a portion of the FOV 18 in the corresponding direction of the FOV 18, reconstruction conditions may vary depending on the directions of X-ray emissions. Thus, the X-ray imaging method according to the present invention uniformly adjusts the reconstruction conditions depending on the positions of the FOV 18, and this feature forms another characteristic of the present invention.

More specifically, minimum units of an X-ray 3D image are voxels, and the reconstruction may be regarded as a series of processes of obtaining CT numbers or Hounsfield units (Hus) of the voxels located on routes through which X-rays pass. Referring to a specific voxel, the CT number or HU of the voxel based on the result of the detection of X-rays that have passed through the voxel in several directions. For this, in X-rays that have passed through the voxel in several directions, reconstruction conditions for the voxel, for example, a magnification ratio and a degree of X-ray overlapping, must be uniform.

However, reconstruction conditions may vary according to the positions of the FOV 18, since the X-ray imaging method according to the present invention uses results of the detection of X-rays that have passed through portions of the FOV 18 in several directions of the FOV 18. For example, FIG. 12 is a conceptual view illustrating differences in the magnification ratio of the detection result of X-rays and the position-specific degree of X-ray overlapping in the FOV 18 in the X-ray imaging method according to the present invention.

Figure 12:
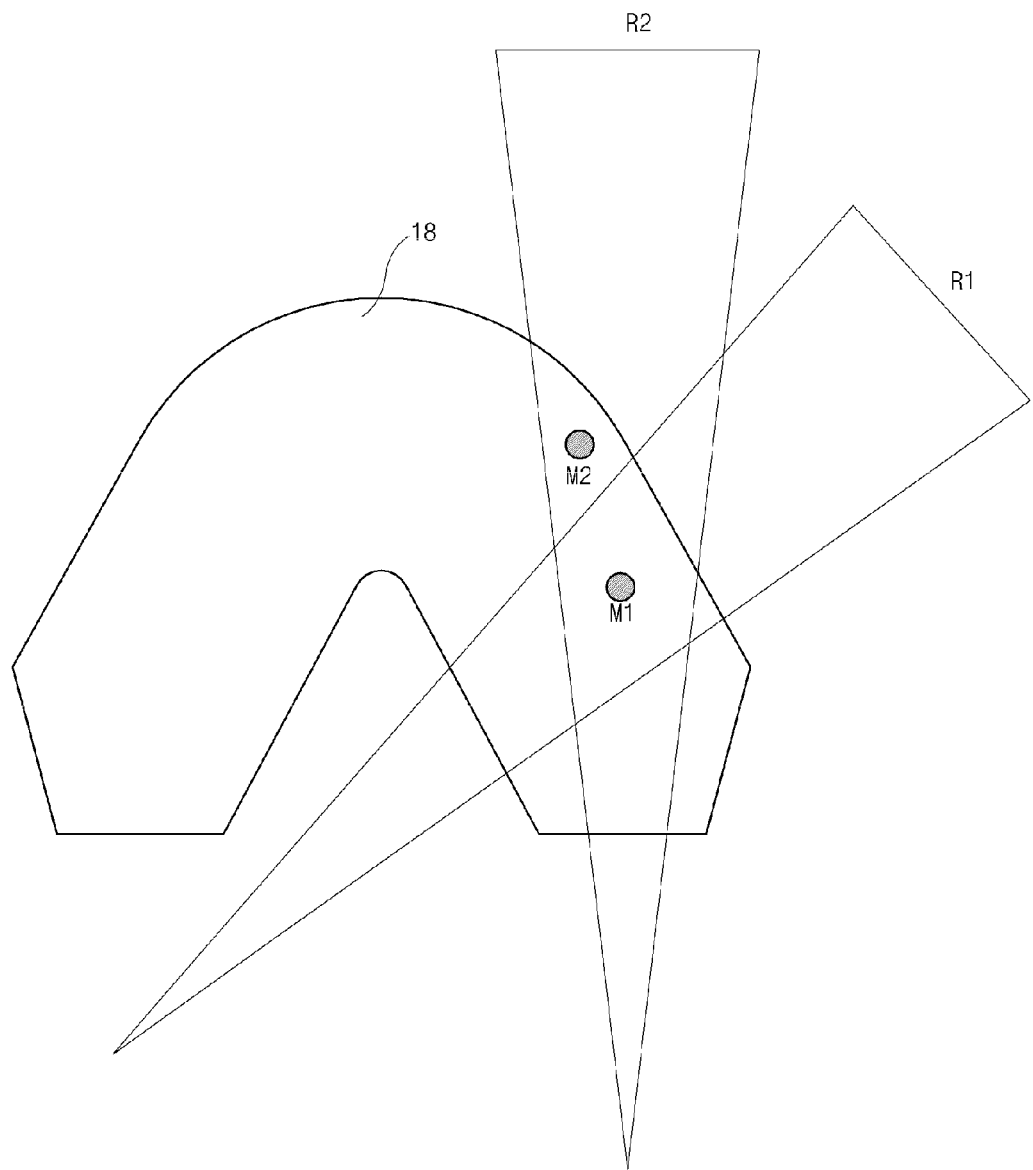
FIG. 12 is a conceptual view illustrating differences in the magnification ratio of the detection result of X-rays and the degree of X-ray overlapping in the FOV according to directions of X-ray emissions.

As illustrated in FIG. 12, when X-ray images are obtained in two positions using the X-ray imaging method according to the present invention, X-rays that have passed through one point M1 within the FOV 18 are obtained by detecting X-rays in positions R1 and R2. Here, the X-ray imaging method according to the present invention projects the directions of X-ray emissions to at least one curved track, such that the distance between M1 and R1 may differ from the distance between M1 and R2. Thus, the results of the detection of X-rays at the same point in the FOV 18 may have different magnification ratios according to the directions of X-ray emissions. In the same manner, although X-rays that have passed through a point M1 in the FOV 18 form results of X-ray detection in the positions R1 and R2, X-rays that have passed through a point M2 in the FOV 18 are detected only in R2. Thus, even though M1 and M2 are formed from the same material, the voxels may have different CT numbers or HUs.

Accordingly, the X-ray imaging method according to the present invention compensates for the magnification ratios of the results of X-ray detection according to the directions of X-ray emissions during or prior to the reconstruction process and degrees of X-ray overlapping in the FOV 18 according to the directions of X-ray emissions, thereby causing the position-specific reconstruction conditions of the FOV 18 to be uniform. In addition, a 3D image of the FOV 18 is rendered through the reconstruction process using a reconstruction algorithm.

Figure 13:
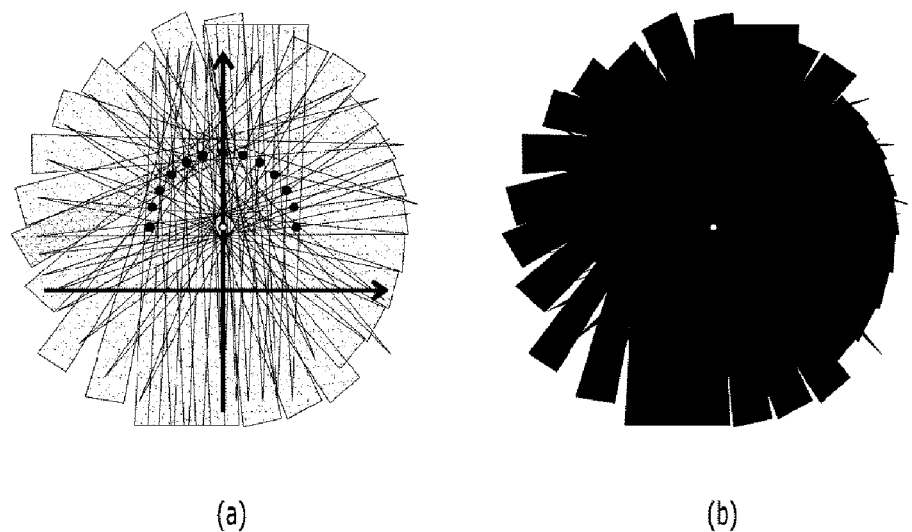
FIG. 13 is a conceptual view illustrating before and after compensation for degrees of X-ray overlapping in an FOV.

For reference, FIG. 13 is a conceptual view illustrating the process of compensating for degrees of X-ray overlapping according to directions of X-ray emissions in the X-ray imaging method according to the present invention. Referring to the left part (a) of FIG. 13, X-rays that have passed through portions of the FOV 18 in several directions of the FOV 18 exhibit different degrees of overlapping according to the positions of the FOV 18. In contrast, when the degrees of X-ray overlapping in the FOV 18 are compensated for according to the directions of X-ray emissions in the X-ray imaging method according to the present invention, the position-specific degrees of X-ray overlapping of the FOV 18 can be uniformized, as illustrated in the right part (b) of FIG. 13.

Figure 14:
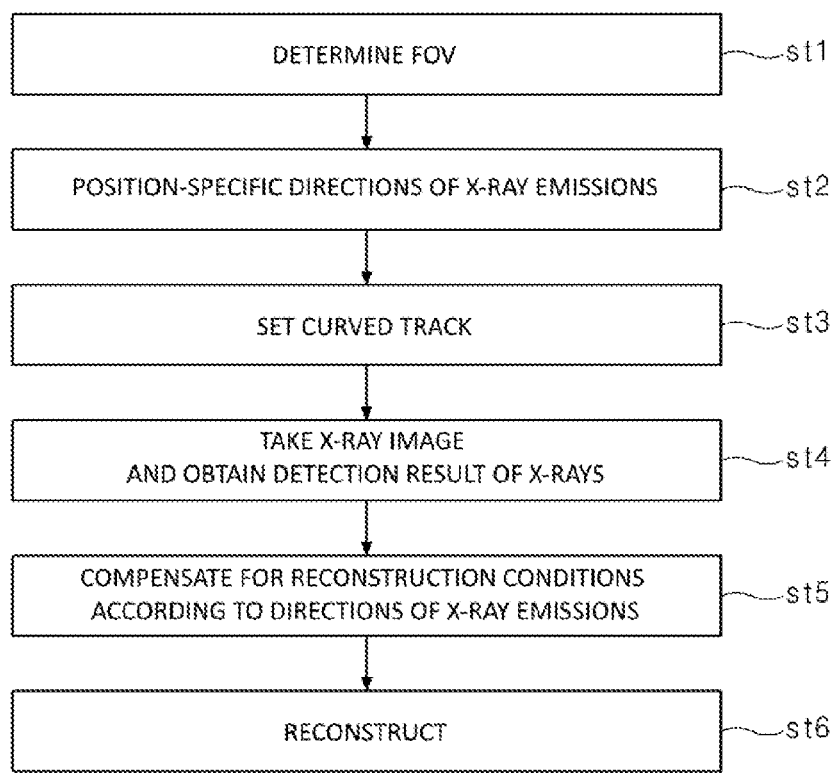
FIG. 14 is a flowchart illustrating an X-ray imaging method according to the present invention.

Hereinafter, the X-ray imaging method according to the present invention described above will be described sequentially with reference to FIG. 14. FIG. 14 is a flowchart illustrating the X-ray imaging method according to the present invention.

First, the X-ray imaging method according to the present invention determines an FOV considering the purpose of image obtaining or the like (st1).

Here, the cross-section perpendicular to the longitudinal direction of the FOV may have the shape of a variety of diagrams, such as a circle, an ellipse, and an arc. The X-ray sensor for X-ray imaging of the FOV exhibits a small width less than the radius of a smallest circle, including the FOV, multiplied by the magnification ratio, and the X-ray source and the X-ray sensor are fixed to both ends of the rotary arm, which can move and rotate on the rotation shaft between the X-ray source and the X-ray sensor.

Afterwards, the X-ray imaging method according to the present invention defines position-specific directions of X-ray emissions for 3D imaging of the FOV (st2).

Here, the position-specific directions of X-ray emissions are determined to satisfy a range of directions of X-ray emissions required for 3D image reconstruction of the FOV, considering X-rays passing through the FOV in all directions.

Thereafter, the X-ray imaging method according to the present invention sets at least one curved track (st3). In addition, the position-specific directions of X-ray emissions required for 3D image reconstruction of the FOV are projected to the curved track.

Here, when the position-specific directions of X-ray emissions required for 3D image reconstruction of the FOV are extended in corresponding directions, the curved track may be at least one track that substantially all of the position-specific directions of X-ray emissions cross. The number or shape of the curved track is not substantially limited. However, considering that the curved track is the track on which the rotary shaft between the X-ray source and the X-ray sensor rotates and moves, the curved track needs to be designed to remove the possibility of physical interference, such as collision, with a subject, maximize the ease of control in response to mechanical movement of the X-ray source and the X-ray sensor, and minimize any factors, such as vibration, that may lower the reliability of X-ray images. Thus, the curved track represents concentric circles, including two or less circular tracks having different sizes, or similar shapes. The movement and rotation of the rotary shaft on each of the circular tracks are defined in a single direction without conversion to the opposite direction.

Afterwards, the X-ray imaging method according to the present invention determines at least one curved track as the track of movement of the rotary shaft between the X-ray source and the X-ray sensor, and obtains X-ray images in the directions of X-ray emissions projected to the curved track by properly rotating the X-ray source and the X-ray sensor while moving the rotary shaft along the curved track, thereby obtaining results of detection of X-rays that have passed through portions of the FOV (st4).

Thereafter, the X-ray imaging method according to the present invention adjusts magnification ratios of the results of detection of X-rays and position-specific degrees of X-ray overlapping of the FOV based on reconstruction conditions according to the directions of X-ray emissionss (st5), and finally renders a 3D image of the FOV through reconstruction using a reconstruction algorithm (st6).

In order to render the 3D image of the FOV using the X-ray imaging method according to the present invention, the rotary shaft between the X-ray source and the X-ray sensor must be able to rotate while moving on the curved track. Accordingly, the present invention provides an X-ray imaging device, in which the rotary shaft thereof the X-ray source and the X-ray sensor is movable while rotating on the curved track in at least predetermined section during X-ray image obtaining.

Hereinafter, embodiments of the X-ray imaging device according to the present invention will be described.

Figure 15:
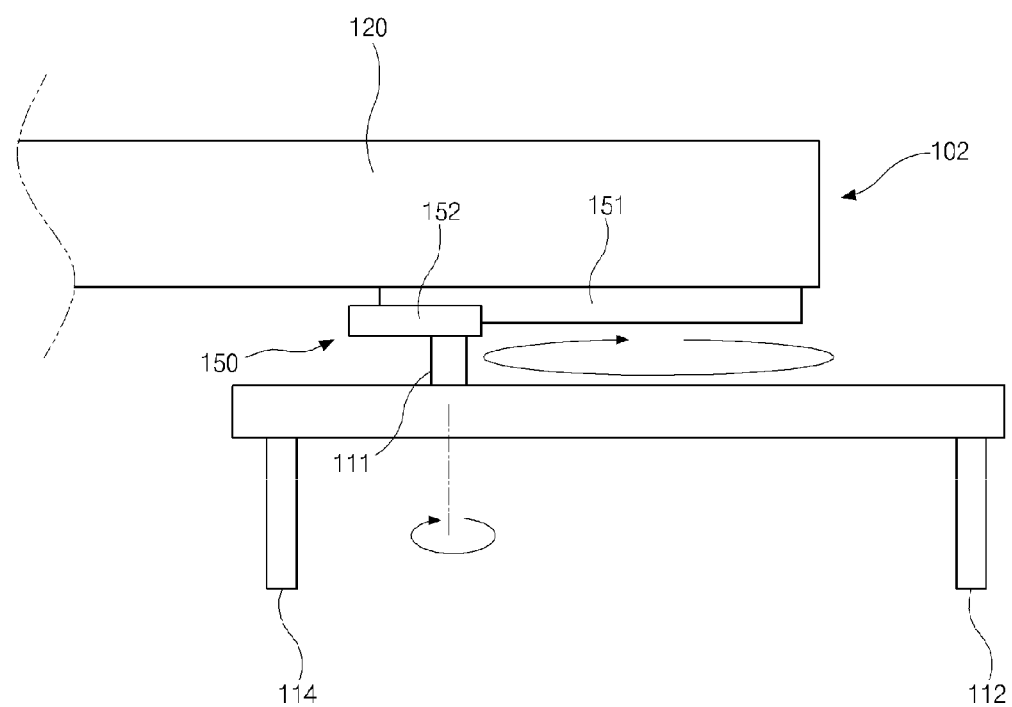
FIG. 15 is a side-elevation view illustrating an X-ray imaging device according to an embodiment of the present invention.
Figure 16:
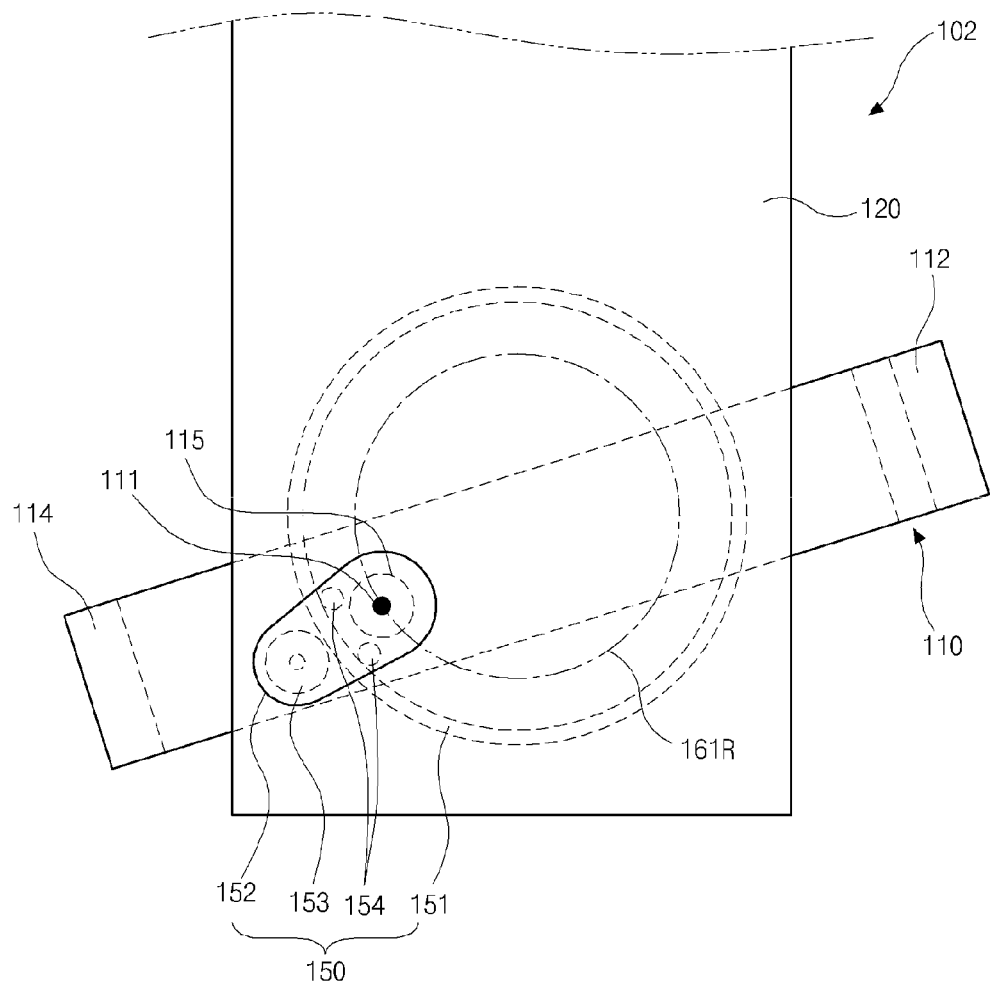
FIG. 16 is a top-plan view illustrating the X-ray imaging device according to the embodiment of the present invention.

FIG. 15 and FIG. 16 are top-plan and side-elevation views illustrating a part of an X-ray imaging device according to an embodiment of the present invention. In FIG. 15 and FIG. 16, only a part of an image-obtaining unit 102 including an X-ray source 112 and an X-ray sensor 114 is illustrated for the sake of brevity.

As illustrated in the drawings, the image-obtaining unit 102 of the X-ray imaging device according to the present embodiment includes a rotary arm 110 supporting the X-ray source 112 and the X-ray sensor 114, a rotary arm support 120 supporting the rotary arm 110, and a rotary arm-moving unit 150. The rotary arm-moving unit 150 causes the rotary arm 110 to be rotatable and movable with respect to the rotary arm support 120 while connecting the rotary arm 110 to the rotary arm support 120.

The rotary arm 110 has the shape of a gantry or a similar shape, and the X-ray source 112 and the X-ray sensor 114 are disposed on both ends of the rotary arm 110 to face each other. In addition, a rotary shaft 111 is disposed on the rotary arm 110, between the X-ray source 112 and the X-ray sensor 114.

Figure 17:
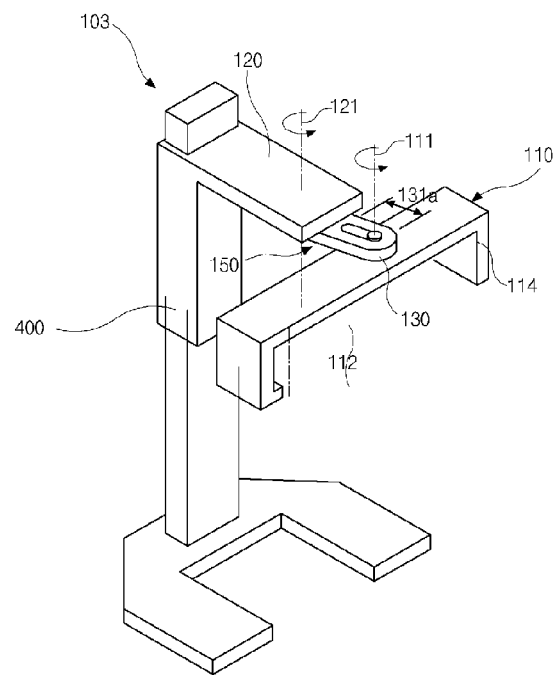
FIG. 17 is a perspective view illustrating an X-ray imaging device according to another embodiment of the present invention.

Referring to FIG. 17, the rotary arm support 120 is connected to a column 400 such that the rotary arm support 120 crosses the column 400. The rotary arm support 120 can be lifted up and down following the column 400, and supports the rotary arm 110 by means of the rotary arm-moving unit 150.

The rotary arm-moving unit 150 causes the rotary arm 111 of the rotary arm 110 to be rotatable and movable with respect to the rotary arm support 120 while connecting the rotary arm 110 to the rotary arm support 120. In this regard, the rotary arm-moving unit 150 includes a curved rail 151 defining a curved track and a movable base 152 movable on the curved rail 151. The movable base 152 is rotatably connected to the rotary shaft 111 of the rotary arm 110.

The curved rail 151 may be disposed on the rotary arm support 120. The movable base 152 includes a rotary arm driving unit 115 to rotate the rotary shaft 111 and a travel driving unit 153 to move the movable base 152 on the curved rail 151. In addition, it is preferable guide rollers 154 are disposed to face the travel driving unit 153, with the curved rail 151 being situated between the guide rollers 154 and the travel driving unit 153. The guide rollers 154 guide the movable base 152 such that the movable base 152 can move on the curved rail 151.

An example of the travel driving unit 153 may include a pulley in rolling contact with a motor and the curved rail 151. In another example, when the curved rail 151 has a rack on the outer circumference thereof, the travel driving unit 153 may include a pinion engaged with the rack. In addition, an example of the rotary arm driving unit 115 may include a motor, and as required, a gear transferring rotating force of the motor to the rotary shaft 111 of the rotary arm 110.

As illustrated in the drawings, the curved rail 151 defines the curved track, i.e. a route on which the rotary shaft 111 moves. In addition, the movable base 152 causes the rotary shaft 111 to move on the curved track defined by the curved rail 151. The movement of the rotary shaft 111 can be executed together with the rotation of the rotary shaft 111. Here, the term "executed together" includes a simultaneous case or a sequential case. Accordingly, the rotary shaft 111 moves and rotates on the curved track defined by the curved rail 151, in at least a predetermined section during X-ray image picturing.

The curved rail 151 is not limited to the circle unlike the drawings, and may be a closed curve, such as a circle or an ellipse, in which the starting point meets the endpoint, or an open curve, in which the starting point is separated from the endpoint. That is, the shape of the curved rail 151 may be designed along the curved track of the rotary shaft 111, as described above.

Accordingly, in the X-ray imaging device according to the present embodiment of the present invention, the rotary shaft 111 between the X-ray source 112 and the X-ray sensor 114 can move and rotate on the curved track in at least a predetermined section during X-ray image picturing, and the X-ray source 112 and the X-ray sensor 114 can emit and detect X-rays passing through portions of the FOV with respect to the entire area of the FOV, in several directions of the FOV.

FIG. 17 is a perspective view illustrating an X-ray imaging device according to another embodiment of the present invention.

Comparing to the former embodiment, the image-obtaining unit 102 according to the present embodiment is characterized in that the rotary arm-moving unit 150 connecting the rotary arm support 120 and the rotary arm 110 includes a connecting arm 130.

One portion of the connecting arm 130 is connected to the rotary shaft 111, such that the rotary arm 110 can rotate around the rotary shaft 111 with respect to the connecting arm 130. The other portion of the connecting arm 130 is connected to the rotary arm support 120 by means of the connecting shaft 121, such that the connecting arm 130 can rotate around the connecting shaft 121 with respect to the rotary arm support 120.

In this regard, although not shown in the drawings, the rotary arm support 120 may include a driving unit to rotate the connecting shaft 121 of the connecting arm 130. The connecting arm 130 or the rotary arm 110 may include another driving unit to rotate the rotary shaft 111.

Here, it is preferable that the connecting arm 130 may have a shaft-adjusting portion 131a able to move at least one of the rotary shaft 111 and the connecting shaft 121. For example, the shaft-adjusting portion 131a adjusts the distance between the rotary shaft 111 and the connecting shaft 121 by moving at least one of the two shafts in the longitudinal direction of the connecting arm 130. The curved track, i.e. the track on which the rotary shaft 111 moves during X-ray image obtaining, can be variously adjusted using the shaft-adjusting portion 131a.

Consequently, in the X-ray imaging device according to the present embodiment, the rotary shaft 111 between the X-ray source 112 and the X-ray sensor 114 can move and rotate on the curved track in at least a predetermined section during X-ray image obtaining. The X-ray source 112 and the X-ray sensor 114 can emit and detect X-rays passing through portions of the FOV with respect to the entire area of the FOV, in several directions of the FOV.

Figure 18:
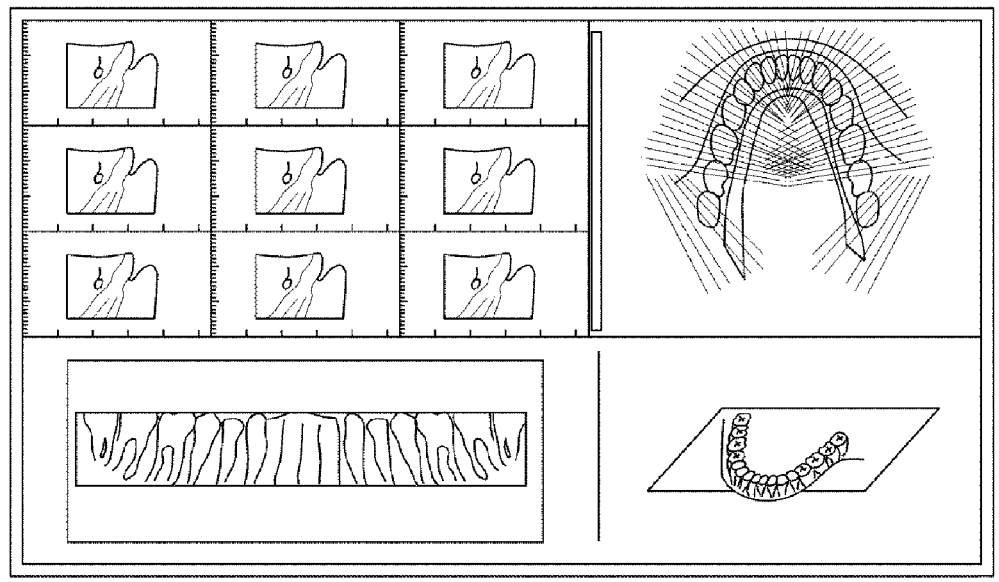
FIG. 18 is a view illustrating a result of X-ray imaging according to the present invention.

FIG. 18 illustrates a 3D image of an FOV rendered using the X-ray imaging method or the X-ray imaging device according to the present invention. Although not illustrated in separate drawings, the X-ray imaging device according to the present invention may include a display device in order to display the 3D image. Alternatively, the 3D image may be displayed on a separate display device, such as a computer, connected to the X-ray imaging device according to the present invention via a wired or wireless medium.

As illustrated in the drawings, the display device can display the 3D image of the FOV (refer to the bottom right part), and can provide a variety of tomographic images according to positions and directions desired by a user. For example, when the FOV has the shape of an arch or a horse's hoof including the dental arch of a subject, a 3D image of the dental arch of the subject can be displayed on the display device, and a variety of tomographic images can be displayed together in the 3D image.

Here, it is preferable that the image processor or the separate computer may have a computer program installed therein in order to display X-ray tomographic images representing the entire track of the dental arch on the display device, based on a position of the 3D image designated by a user using an input part or the like. Panoramic cross-sections perpendicular to the track in the X-ray tomographic images designated by the user may be displayed on the display device.

The panoramic cross-sections are standard images most familiar to dentists, and are converted from the 3D image. Thus, the panoramic cross-sections have very accurate information regarding lengths, with no drawbacks, such as teeth overlapping and blurring caused by the cervical vertebrae, which would otherwise be formed on existing transmission images. Accordingly, the applicability thereof is extensive.

The foregoing descriptions and drawings have been presented by way of example for the purposes of illustration, and are not intended to limit the technical principle of the present invention. A variety of modifications or applications of the embodiments of the present invention are possible without from the technical principle of the present invention. Such modifications or applications should be understood to belong to the scope of the present invention, which shall be defined by the accompanying claims and equivalents thereof.

The invention claimed is:

1. An X-ray imaging device comprising:
   an X-ray source configured to emit X-rays to a portion of a field of view;
   an X-ray sensor configured to detect the X-rays that have passed through the portion of the field of view, and wherein the X-ray sensor has a width less than a radius of a smallest circle including a cross-section perpendicular to a longitudinal direction of the field of view multiplied by a magnification ratio;
   a moving unit configured to move at least one of the X-ray source and the X-ray sensor such that the X-ray source emits the X-rays in several directions of the field of view to pass through substantially the entire portions of the field of view and the X-ray sensor receives the X-rays that have passed through substantially the entire portions of the field of view; and
   an imaging processor configured to render a three-dimensional image of the entire field of view based on X-rays that have passed through substantially the entire portions of the field of view and have been detected by the X-ray sensor.

2. The X-ray imaging device according to claim 1, wherein the moving unit includes a rotary arm configured to mount the X-ray source and the X-ray sensor such that the X-ray source and the X-ray sensor are disposed on both sides of the field of view to face each other, wherein the rotary arm rotates around a rotary shaft locating between the X-ray source and the X-ray sensor.

3. The X-ray imaging device according to claim 2, wherein the moving unit comprises a rotary arm-moving unit configured to move the rotary shaft on a plane perpendicular to the rotary shaft during X-ray image obtaining.

4. The X-ray imaging device according to claim 3, wherein the rotary arm-moving unit configured to move the rotary shaft on a curved track on the plane.

5. The X-ray imaging device according to claim 1, wherein the X-ray source emits X-rays in position-specific directions such that a range of angles of X-ray emissions in each position of the field of view is equal to or greater than a reference value.

6. The X-ray imaging device according to claim 5, wherein the reference value is equal to or greater than 90°.

7. The X-ray imaging device according to claim 5, wherein the reference value is equal to or greater than 180°.

8. The X-ray imaging device according to claim 1, wherein the detected X-rays are compensated by degrees of X-ray overlapping.

9. An X-ray imaging device comprising:
   an X-ray source configured to emit X-rays to a portion of a field of view, wherein the portion of the field of view is less than a half of the field of view;
   an X-ray sensor detecting the X-rays that have passed through the portion of the field of view;
   a rotary arm configured to mount the X-ray source and the X-ray sensor such that the X-ray source and the X-ray sensor are disposed on both sides of the field of view to face each other, and to rotate around a rotary shaft between the X-ray source and the X-ray sensor; and
   a rotary arm-moving unit configured to move the rotary shaft on a plane perpendicular to the rotary shaft in at least a section of X-ray image obtaining.

10. The X-ray imaging device according to claim 9, wherein the rotary arm-moving unit moves the rotary shaft such that the X-ray source emits the X-rays in several directions of the field of view to pass through substantially entire portions of the field of view and the X-ray sensor receives the X-rays that have passed through substantially the entire portions of the field of view.

11. The X-ray imaging device according to claim 9, further comprising a rotary arm support configured to support the rotary arm by means of the rotary arm-moving unit.

12. The X-ray imaging device according to claim 11, wherein the rotary arm-moving unit includes:
    a movable base connected to the rotary arm and rotatably disposed on the rotary arm support;
    a first driving unit configured to move the movable base with respect to the rotary arm support such that the rotary shaft moves on a curved track; and
    a second driving unit configured to rotate the rotary shaft with respect to the movable base.

13. The X-ray imaging device according to claim 12, wherein the rotary arm-moving unit further includes a curved rail disposed on the rotary arm support, the movable base being movable on the curved rail.

14. The X-ray imaging device according to claim 11, wherein the rotary arm-moving unit includes:
    a connecting arm connected to the rotary arm and connected to the rotary arm shaft by means of a connecting shaft;
    a first driving unit configured to rotate the connecting shaft with respect to the rotary arm support such that the rotary shaft moves on a curved track; and
    a second driving unit configured to rotate the rotary shaft with respect to the connecting arm.

15. The X-ray imaging device according to claim 14, further comprising a shaft-adjusting portion configured to move at least one of the connecting shaft and the rotary shaft with respect to the connecting arm.

16. The X-ray imaging device according to claim 15, wherein the shaft-adjusting portion configured to adjust a distance between the connecting shaft and the rotary shaft.

17. The X-ray imaging device according to claim 9, wherein the X-ray sensor has a width less than a radius of a smallest circle, including a cross-section perpendicular to a longitudinal direction of the field of view, multiplied by a magnification ratio.

18. An X-ray imaging device comprising:
    an X-ray source configured to emit X-rays to a portion of a field of view, wherein the portion of the field of view is less than a half of the field of view;
    an X-ray sensor configured to detect the X-rays that have passed through the portion of the field of view;
    a moving unit configured to move at least one of the X-ray source and the X-ray sensor such that the X-ray source emits the X-rays in several directions of the field of view to pass through substantially the entire portions of the field of view and the X-ray sensor receives the X-rays that have passed through substantially the entire portions of the field of view; and
    an imaging processor configured to render a three-dimensional image of the entire field of view based on X-rays that have passed through substantially the entire portions of the field of view and have been detected by the X-ray sensor.

* * * * *